United States Patent [19]

Pond et al.

[11] 4,029,670
[45] June 14, 1977

[54] POLYCHROMOPHORIC HETEROCYCLIC ULTRAVIOLET STABILIZERS

[75] Inventors: David M. Pond; William C. Dickason; Edward U. Elam, all of Kingsport, Tenn.

[73] Assignee: Eastman Kodak Company, Rochester, N.Y.

[22] Filed: Sept. 19, 1975

[21] Appl. No.: 615,033

[52] U.S. Cl. .......................... 260/308 B; 106/176; 260/45.8 NT; 260/45.8 NZ; 260/304 R; 260/307 D; 260/309.2; 260/326.13 R

[51] Int. Cl.$^2$ ..................................... C07D 249/20

[58] Field of Search ............................. 260/308 B

[56] References Cited

UNITED STATES PATENTS

| | | | |
|---|---|---|---|
| 3,936,418 | 2/1976 | Pond et al. | 260/308 B |
| 3,954,706 | 5/1976 | Wang et al. | 260/308 B |

Primary Examiner—Paul M. Coughlan, Jr.
Attorney, Agent, or Firm—Edward R. Weber; Daniel B. Reece, III

[57] ABSTRACT

The invention relates to bichromophoric heterocyclic ester compounds which have been found to be effective ultraviolet stabilizers. The invention also relates to ultraviolet degradable organic compositions containing a stabilizing amount of these bichromophoric heterocyclic ester compositions to prevent such degradation. These stabilizers are effective in the presence of other additives commonly employed in polymeric compositions including, for example, pigments, colorants, fillers, reinforcing agents and the like. These ultraviolet stabilizers may also be incorporated into the organic compositions in the polymer melt or dissolved in the polymer dope, coated on the exterior of the molded article, film or extruded fiber.

8 Claims, No Drawings

POLYCHROMOPHORIC HETEROCYCLIC ULTRAVIOLET STABILIZERS

This invention relates to bichromophoric heterocyclic ester ultraviolet stabilizers and their use in organic compositions. More particularly, the invention relates to bichromophoric heterocylic ester compositions and the stabilization of ultraviolet degradable organic compositions against deterioration resulting from the exposure to such radiations with such bichromophoric heterocyclic ester compositions.

The degradative effects of ultraviolet light on various organic compositions is well known in the art. The photo-deterioration or degradation is of particular concern with organic photo-degradable compositions which are exposed to ultraviolet light, such as sunlight, for long periods of time. One group of such photo-degradable organic compositions are polymeric compositions such as polyolefins, polyesters and the like. On exposure to sunlight for extended periods of time, these polymeric compositions degrade and their physical properties are reduced to render the polymeric composition less useful for most applications. Therefore, considerable effort has been directed to providing a solution to the photo-degradation problem of polymeric compositions. As a result of this effort, there have been discovered many additives and stabilizers which improve the stability of polymeric compositions.

Moreover, various additives and stabilizers exhibit the power to absorb ultraviolet radiation within the band of 2900 to 4000 A. and, when incorporated in various plastic materials such as transparent sheets, the resultant sheet acts as a filter for all the radiation passing through and will transmit only such radiations as are not absorbed by the sheet and/or the absorbing agent. It is thus possible to screen out undesirable radiations and utilize the resulting transparent sheet as a filter in many technical and commercial applications, such as wrappings for food products and the like.

While there are many additives, stabilizers and mixtures thereof which are known in the art to improve the ultraviolet light stability of organic compositions, there is a need in the art for more efficient and effective stabilizers to prevent the photo-degradation of organic compositions susceptible to photo-degradation. Therefore, to provide a more effective and efficient ultraviolet stabilizer for organic compositions susceptible to such degradation would be an advance in the state of the art.

It is, therefore, an object of the present invention to provide more effective and efficient ultraviolet light stabilizer compositions.

Another object of the present invention is to provide useful compositions characterized by improved resistance to ultraviolet degradation and deterioration.

It is still another object of the present invention to provide compositions containing bichromophoric compositions which are resistant to ultraviolet degradation.

It is a still further object of this invention to provide processes for improving the resistance of organic materials to deterioration and degradation by actinic radiation and especially ultraviolet radiation.

It is a still further object of this invention to provide compositions and processes for improving the resistance of organic materials to deterioration and degradation by actinic radiations, including short wavelength visible radiations.

Further objects and advantages of the invention will be apparent to those skilled in the art from the accompanying disclosure and claims.

In accordance with the present invention, bichromophoric heterocyclic ester compositions are provided which are useful as ultravilet stabilizers or ultraviolet screening agents. These organic compositions contain at least one heterocyclic group containing composition connected through a carboxyl group to an aromatic ring which, upon exposure to ultraviolet light, may undergo the "photo-Fries" rearrangement. The polychromophoric compositions of the present invention have the following structure:

$$(A)_x-C$$

wherein A is a group having the structure:

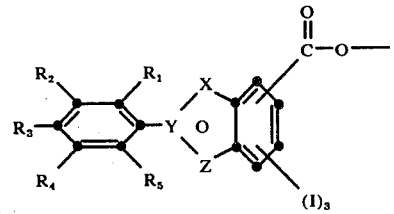

wherein
X and Y are a carbon atom, a carbon atom containing an R group, or a nitrogen atom;
Z is an oxygen atom, a sulfur atom, a nitrogen atom, a nitrogen atom containing a hydrogen atom or a substituted or unsubstituted lower alkyl group having 1 to 12 carbon atoms;
R, $R_1$, $R_2$, $R_3$, $R_4$ and $R_5$ are hydrogen, lower alkyl, substituted lower alkyl, cycloalkyl, substituted cycloalkyl, aryl, halogen, substituted aryl, lower alkylaryl, aryl-substituted-aryl, alkoxy, carboxy, nitrile, and the substituents $R_1$ and $R_2$, $R_2$ and $R_3$, and $R_3$ and $R_4$, combined with the carbon atoms to which they are attached, are joined alkylene groups completing a carboxylic ring which can be substituted with any of the substituents listed above for $R_1$, $R_2$, $R_3$ and $R_4$.

I is a substituent listed above for $R_1$, $R_2$, $R_3$ and $R_4$ and is present on all positions of the benzenoid ring, except the carbon atom attached to the heterocyclic ring and the carbon atom attached to the carboxyl group connecting the heterocylic aromatic A group with the aromatic C group. At least one I substituent on one of the carbon atoms adjacent to the carbon atom attached to the carbonyl group is hydrogen and the remaining I substituents can all be the same or different.

x is an integer of 1 to 4; and
C is:
a. an aromatic group having the formula

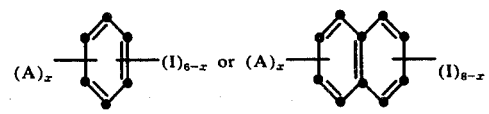

where I is the same substituent as listed above and is present in all positions of the benzenoid ring except the carbon atom attached to the carbonyl group connecting the A and C moieties, and said I substituents can all be one of the substituents listed above or different listed substituents;
  b. an alkyl group or hydrogen; and
  c. an aromatic group having the formula

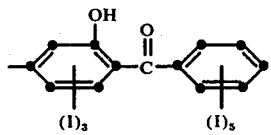

Suitable A groups having the structure

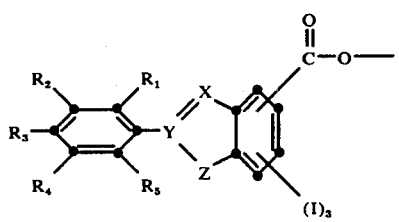

are, for example, substituted and unsubstituted benzoxazoles, benzotriazoles, benzothiazoles, and benzimidazoles.

Examples of such suitable benzoxazole moieties are those having the formula

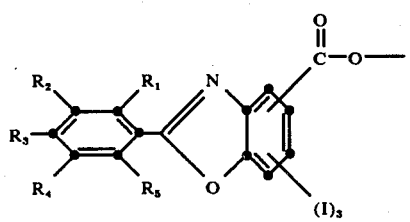

such as 2-(4-methylphenyl)-5-benzoxazolecarboxylate, 2-(3-methylphenyl)-5-benzoxazolecarboxylate, 2-(4-chlorophenyl)-5-benzoxazolecarboxylate, 2-(4-dimethylaminophenyl)-5-benzoxazolecarboxylate, 2-(4-t-butylphenyl)-5-benzoxazolecarboxylate, 2-(4-methoxyphenyl)-5-benzoxazolecarboxylate, 2-(4-methylphenyl)-6-methyl-5-benzoxazolecarboxylate, 2-(4-chlorophenyl)-6-methyl-5-benzoxazolecarboxylate, 2-(4-methylphenyl-6-chloro-5-benzoxazolecarboxylate, and 2-(4-methylphenyl)-6-t-butyl-5-benzoxazolecarboxylate.

Examples of suitable benzotriazole moieties are those having the formula

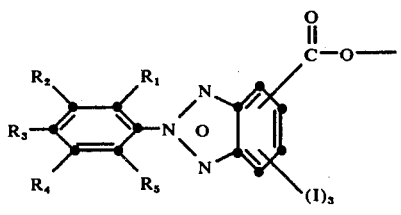

such as 2-(4-methylphenyl)-5-benzotriazolecarboxylate, 2-(4-chlorophenyl)-5-benzotriazolecarboxylate, 2-(4-dimethylaminophenyl)-5-benzotriazolecarboxylate, 2-(3-methylphenyl)-5-benzotriazolecarboxylate, 2-(2-methylphenyl)-5-benzotriazolecarboxylate, and 2-(4-t-butylphenyl)-5-benzotriazolecarboxylate.

Examples of suitable benzothiazole moieties are those having the formula

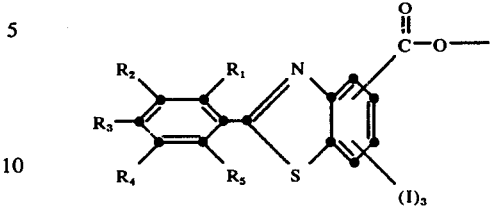

such as 2-(4-methylphenyl)-5-benzothiazolecarboxylate, 2-(4-chlorophenyl)-5-benzothiazolecarboxylate, 2-(3-methoxyphenyl)-5-benzothiazolecarboxylate, 2-(4-methylphenyl)-6-chloro-5-benzothiazolecarboxylate, and 2-(4-chlorophenyl)-6-methyl-5-benzothiazolecarboxylate.

Examples of suitable benzimidazole moieties are those having the formula

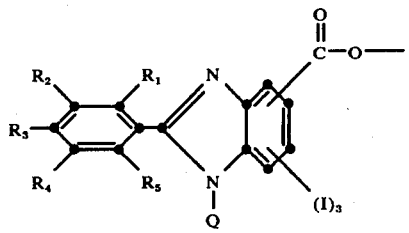

wherein Q is hydrogen or a substituted or unsubstituted lower alkyl group containing 1 to 12 carbon atom such as 2-(4-methylphenyl)-5-benzimidazolecarboxylate, 2-(4-chlorophenyl)-5-benzimidazolecarboxylate, 2-(4-methylphenyl)-6-benzimidazolecarboxylate, 2-(4-methoxyphenyl)-5-(N-ethylbenzimidazole)carboxylate, and 2-(4-methoxyphenyl)-6-chloro-5-(N-methylimidazole)carboxylate.

Examples of suitable indole moieties are those having the formula

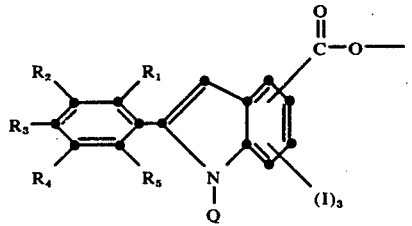

wherein Q is hydrogen or a substituted or unsubstituted lower alkyl containing 1 to 12 carbon atoms, such as 2-(4-methylphenyl)-5-indolecarboxylate, 2-(4-chlorophenyl)-5-indolecarboxylate, 2-(3-methylphenyl)-6-indolecarboxylate, 2-(4-methylphenyl)-6-chloro-5-indolecarboxylate, 2-(4-methypheny)-5-N-methylindole)carboxylate, and 2-(4-chlorophenyl)-6-methyl-5-(N-ethylindole)carboxylate.

Suitable C groups are those which are
  a. an aromatic group having the formula

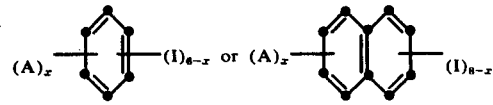

where I is the same substituent as listed above and is present in all positions of the benzenoid ring except the carbon atom attached to the carbonyl group connecting the A and C moieties, and said I substituents can all be one of the substituents listed above or different listed substituents;

b. an aromatic group having formula

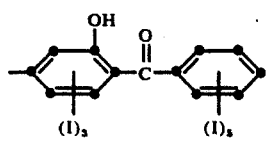

The bichromophoric heterocyclic ester compositions can be prepared by reacting an acid chloride with a phenol. For example, one group of such organic compounds useful as ultraviolet stabilizers is, for example, compositions having the following structures

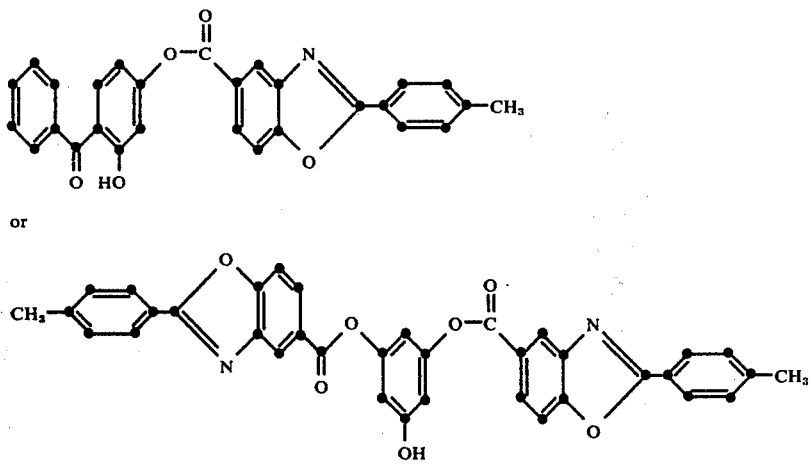

One method for preparing these compounds is by the following procedure:

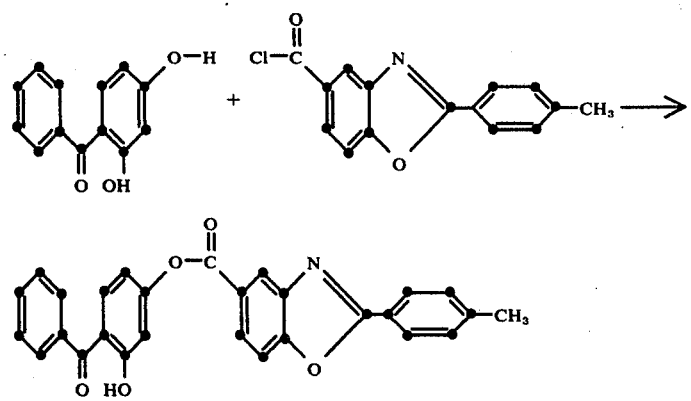

It is necessary that at least one carbon atom adjacent to the carbon atom attached to the carboxy oxygen contain a hydrogen substituent so that on exposure to ultraviolet light, the aryl ester is capable by the photo-Fries rearrangement of forming a phenol group in that position formerly joined through an oxygen atom to the carbonyl linking group, as for example:

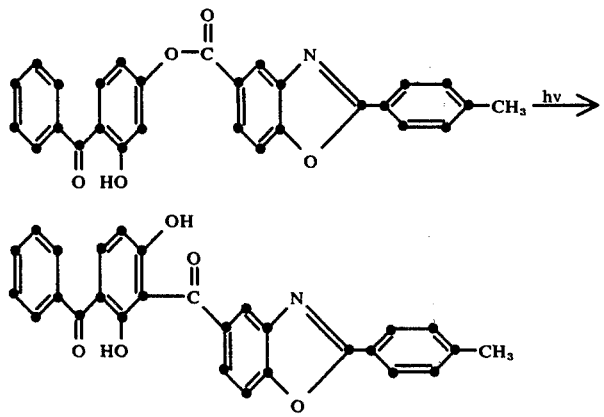

The acid chlorides were prepared by reaction of the corresponding acid [See Zh. Obshch. Khim., 38, 100 1–5 (1968); Chem. Abstr. 69 96568 (1968)] with freshly distilled thionyl chloride [See J. Chem. Soc. 101, 2476 (1912)]. The phenols were obtained from commercial sources, or were prepared by standard methods; a critical requirement is that one of the positions adjacent the phenolic hydroxyl group be unsubstituted.

The heterocyclic compositons can be added to organic compositions which are susceptible to ultraviolet degradation. Such compositions include, for example, polymeric compositions such as polyester fiber and molding compositions, such as polyethlene terephthalate, poly(tetramethylene terephthalate) and the like; polyolefins such as, for example, high, medium and low density polyethylene, polypropylene, polybutene and the like; polyamides such as nylon 6, nylon 66, N-methoxymethyl polyhexamethylene adipamide and the like; polycarbonates; polyvinyl chlorides and copolymers; cellulose esters; acrylic/butadiene/styrene plastic; polyacrylics such as methyl methacrylate; polystyrene; gelatin; vinylidene chloride copolymers such as vinylidene chloride/vinyl acetate copolymers; ethylene vinyl acetate copolymers; cellulose ethers such as methyl cellulose; polyvinyl esters such as polyvinyl acetate; polyethylene oxide; polyvinyl acetals, polyformaldehydes; and polyurethanes. Such compositions also include natural and synthetic rubbers, such as polybutadiene, and unsaturated organic compositions such as oils and the like, as well as compositions containing such organic compositions.

The bichromophoric compositions, as effective ultraviolet stabilizers or screening agents, are generally used in an amount of from 0.01 to 10%, by weight, based on the weight of the organic material to which they are added. While a detectable amount of ultraviolet screening and stabilization may be obtained with amounts less than 0.01%, this amount of stabilization or screening would be of little practical utility in a commercial application. Moreover, while amounts greater than 10%, by weight, provide effective ultraviolet stability and screening, such concentrations are undesirable because of cost and the deleterious effect which such concentrations may have on the mechanical properties of the organic composition in which the stabilizer is incorporated. Preferably, the stabilizer is used in an amount of from about 0.1 to about 3%, by weight. For example, an amount of 2%, by weight, of the stabilizer effectively stabilizes cellulose acetate butyrate and polyester such as poly(tetramethylene terephthalate) plastic compositions.

The ultraviolet stabilized organic compositions of the present invention may also contain other additives, pigments, colorants, stabilizers and the like. For example, polymeric compositions, such as polyolefins, may also contain and generally do contain other additives such as white or colored pigments or colorants, antioxidants, plasticizers, flow aids, processing aids, polymeric modifiers and the like.

These novel bichromophoric ultraviolet stabilizers may be incorporated into organic compositions by melt-blending or may be added onto the surface of an organic plastic material prior to being molded into a suitable object. These materials can also be added to coatings and the like which can be applied to the surface of a molded object.

This invention will be further illustrated by the following examples although it will be understood that examples are included merely for purposes of illustration and are not intended to limit the scope of the invention.

EXAMPLE 1

Methyl 2-(4-methylphenyl)-5-benzoxazolecarboxylate (1a) can be prepared by the following procedure The condensation (and subsequent cyclization) of methyl 4-hydroxy-3-aminobenzoate with p-toluoyl chloride, offered a starting material for the synthesis of a series of bichromophoric stabilizers in which the energy sink is attached directly to the benzoxazole moiety.

EXAMPLE 2

2-(4-Methylphenyl)-5-benzoxazolecarboxylic Acid

A solution containing 16.0 g. (0.06 mole) of methyl 2-(4-methylphenyl)-5-benzoxazolecarboxylate (1a), 4.0 g. (0.1 mole) of sodium hydroxide, and 50 ml. of water in 275 ml. of ethanol was stirred at 25° for 16 hours. The reaction mixture was poured into 1 l. of water. Acidification gave a white precipitate which was filtered, washed with water, and when air-dried amounted to 14.44 g. (95%) of 2-(4-methylphenyl)-5-benzoxazolecarboxylic acid (1b). The ir and nmr spectra were consistent with the proposed structure.

Anal. Calcd. for $C_{15}H_{11}NO_3$ (253.26): C, 71.14; H, 4.38; N, 5.53. Found: C, 70.68; H, 4.37; N, 5.41.

EXAMPLE 3

2-(4-Methylphenyl)-5-benzoxazolecarbonyl Chloride (1c)

2-(4-Methylphenyl)-5-benzoxazole carboxylic acid (13.0 g., 0.05 mole) was heated in 50 ml. of thionyl chloride (containing 10 drops of DMF) for 20 hours. The excess $SOCl_2$ was removed by a nitrogen sparge leaving a white solid. This was recrystallized from toluene to give 12.95 g. (95%) of 2-(4-methylphenyl)-5-benzoxazolyl chloride (1c). The ir and nmr spectra were consistent with the proposed structure.

EXAMPLE 4

Phenyl 2-(4-Methylphenyl)-5-benzoxazolecarboxylate (1d)

A solution containing 4.43 g. (0.016 mole) of 2-(4-methylphenyl)-5-benzoxazolecarbonyl chloride in 50 ml. or methylene chloride was added dropwise to a solution containing 1.88 g (0.02 mole) of phenol and 0.80 g. (0.02 mole) of sodium hydroxide in 25 ml. of water. After stirring at 50° for 20 hours, the layers were separated and the organic layer was dried ($MgSO_4$) and concentrated to give 2.9 g. (54%) of 1d: UV ($CH_2Cl_2$)λ max 306 nm (18,200), $\epsilon_{325}$ = 3500.

Anal. Calcd. for $C_{21}H_{15}NO_3$ (329.36): C, 76,58; H, 4.59; N, 4.25. Found: C, 76,39; H, 4.95; N, 4.12.

EXAMPLE 5

4-Benzoyl-3-hydroxyphenyl 2-(4-Methylphenyl)-5-benzoxazolecarboxylate (1e)

A solution containing 5.42 g. (0.02 mole) of 1c, 4.28 g. (0.02 mole) of 2,4-dihydroxybenzophenone, and 0.8 g. (0.02 mole) of sodium hydroxide in 50 ml. of chloroform and 15 ml. of water was refluxed for 3 hours. After cooling, the layers were separated and the organic layer was concentrated to given 5.27 g. (59%) of 1e as a white crystalline solid: UV (CH$_2$Cl$_2$) λmax 306 nm (31,000), $\epsilon_{325}$ = 18,500.

Anal. Calcd. for C$_{28}$H$_{19}$NO$_5$ (449.47): C, 74.82; H, 4.26; N, 3.12. Found: C, 74.50; H, 4.25; N, 3.30.

EXAMPLE 6 m-Phenylene bis[2-(4-Methylphenyl)-5-benzoxazolecarboxylate] (1f)

A mixture of 1c (5.42 g. 0.02 mole), resorcinol (1.10 g., 0.02 mole), and sodium hydroxide (0.8 g., 0.02 mole) was refluxed for 3 hours in a mixture of chloroform (50 ml.) and water (15 ml.). Upon cooling a solid separated between the layers which was filtered, air-dried, and amounted to 2.43 g. (42%) of 1f. UV (CH$_2$CH$_2$) λmax 306 nm (52,000), $\epsilon_{325}$ = 13,000.

Anal. Calcd. for C$_{36}$H$_{24}$N$_2$O$_2$(580.61): C, 74.47; H, 4.17; N, 4.82. Found: C, 72.91; H, 4.14; N, 4.71.

These polychromophoric compositions find particular utility as ultraviolet stabilizers in organic compositions requiring ultraviolet stability. Such compositions include polymeric compositions such as, for example, polyester fiber and molding compositions, poly-α-olefins, polyamides, acrylics, cellulose esters and the like, as well as molded or shaped articles, film and coatings formed from such materials and the like. Such compositions also include natural and synthetic rubbers, such as natural rubber, as well as organic materials such as oils, fats, and unsaturated organic materials and materials having such materials contained therein such as paints, varnishes, cosmetics and the like.

Weathering data results shown in Table I illustarate the stabilization obtained with the compounds of this invention.

Table I

Weathering of Poly(tetramethylene terephthalate) Containing 0.5% of Various Stabilizers

| Additive (0.5%)[a] | Flatwise Impact Strength After Mercury Lamp Exposure for Hours Indicated, Ft.-Lbs./In.[2] | | |
|---|---|---|---|
| | 0 | 300 | 500 |
| None | 19 | 1 | 1 |
| Methyl-2-(4-Methylphenyl)-5-benzoxazolecarboxylate | 19 | 8 | 1 |
| Phenyl-2-(4-Methylphenyl)-5-benzoxazolecarboxylate | 19 | 15 | 10 |
| 4-Benzoyl-3-hydroxyphenyl-2-(4-methylphenyl)-5-benzoxazolecarboxylate | 19 | 18 | 18 |
| m-Phenylene bis[2-(4-methylphenyl)-5-benzoxazole carboxylate | 19 | 18 | 10 |

[a]Additives were incorporated by blending the powdered stabilizer and granulated polymer followed by extrusion, pelletization and injection molding into 1/16 × 1/2 × 2 1/2 in. flat bars. Flatwise impact strength were determined by ASTM Procedure D256-56 Method A.

The invention has been described in detail with particular reference to preferred embodiments thereof, but it will be understood that variations and modifications can be effected within the spirit and scope of the invention.

We claim:

1. A polychromophoric compound having the formula:

(A)$_x$—C where A is a group having the structure

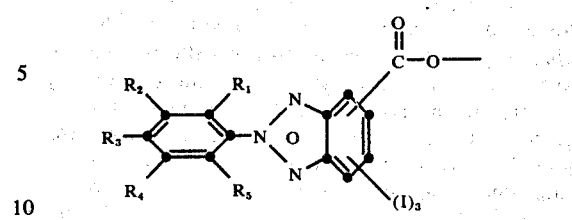

wherein $R_1$, $R_2$, $R_3$, $R_4$ and $R_5$ are hydrogen, chloro, bromo, fluoro, lower alkyl, cycloalkyl, phenyl, lower alkylphenyl, phenyl-substituted-phenyl, alkoxy, phenoxy, dilower alkyl substituted amino, cyano, carboalkoxy and the substituents $R_1$ and $R_2$, $R_2$ and $R_3$, and $R_3$ and $R_4$, combined with the carbon atoms to which they are attached, are joined alkylene groups completing a carbocyclic ring, which ring can also be substituted with one or more of the substituents listed above for $R_1$, $R_2$, $R_3$ and $R_4$;

I is the same as $R_1$, $R_2$, $R_3$ and $R_4$ and is present on all positions of the benzenoid ring, except the carbon atom attached to the heterocyclic ring and the carbon atom attached to the carbonyl group connecting the heterocyclic aromatic A group with the aromatic C group, at least one I substituent on one of the carbon atoms adjacent to said carbon atom attached to said carbonyl group is hydrogen and said remaining I substituents can all be the same or different;

x is an integer of 1 to 4; and

C is:

a. an aromatic group having the formula

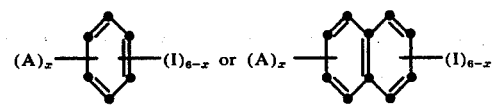

where I is the same substituent as listed above and is present in all positions of the benzenoid ring except the carbon atom attached to the carbonyl group connecting the A and C moieties, and said I substituents can all be one of the substituents listed above or different listed substituents; or b. an aromatic group having the formula

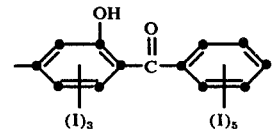

2. A compound according to claim 1 having the formula

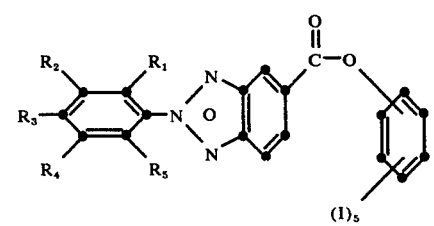

wherein
R₁, R₂, R₃, R₄ and R₅ are hydrogen, chloro, bromo, lower alkyl, cycloalkyl, phenyl, lower alkyl phenyl, alkoxy, phenyloxy, diloweralkyl substituted amino, and cyano, carboalkoxy, and the substituents R₁ and R₂, R₂ and R₃, R₃ and R₄, combined with the carbon atoms to which they are attached, are joined alkylene groups completing a carbocyclic ring, which ring can also be substituted with one or more of the substituents listed above for R₁, R₂, R₃ and R₄;

I is the same as R₁, R₂, R₃ and R₄ and is present on all positions of the benzenoid ring, except the carbon atom attached to the carbonyl linking substituent, at least one of said I substituents on the carbon atom adjacent to said carbon atom attached to said carbonyl group is hydrogen and the remaining I substituents can all be one of the substituents listed above or different listed substituents.

3. A compound according to claim 2 having the formula:

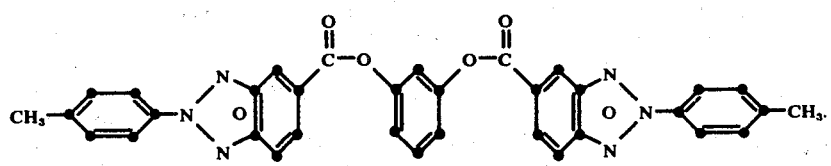

4. A compound according to claim 2 having the formula:

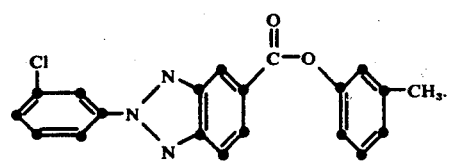

5. A compound according to claim 2 having the formula

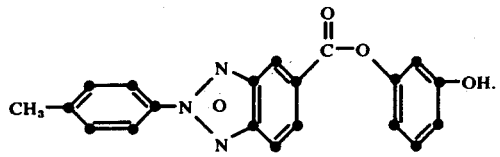

6. A compound according to claim 2 having the formula:

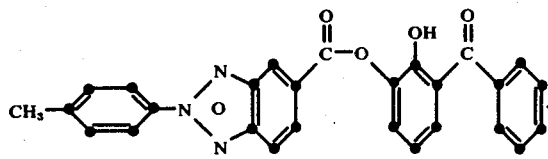

7. A compound according to claim 2 having the formula:

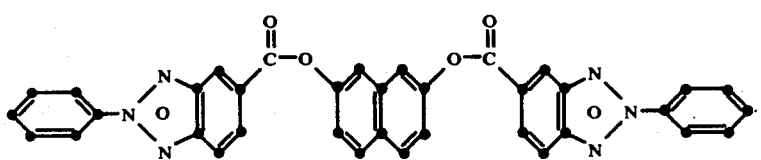

8. A compound according to claim 2 having the formula:

* * * * *